(12) United States Patent
Raadnui

(10) Patent No.: US 8,770,047 B2
(45) Date of Patent: Jul. 8, 2014

(54) APPARATUS AND METHOD FOR PARTICLE ANALYSIS

(75) Inventor: Surapol Raadnui, Nontaburi (TH)

(73) Assignees: The Thailand Research Fund, Bangkok (TH); King Mongkut's University of Technology North Bangkok, Bangkok (TH)

( * ) Notice: Subject to any disclaimer, the term of this patent is extended or adjusted under 35 U.S.C. 154(b) by 80 days.

(21) Appl. No.: 13/386,952

(22) PCT Filed: Jul. 27, 2009

(86) PCT No.: PCT/SG2009/000264
§ 371 (c)(1),
(2), (4) Date: Jan. 25, 2012

(87) PCT Pub. No.: WO2011/014119
PCT Pub. Date: Feb. 3, 2011

(65) Prior Publication Data
US 2012/0118051 A1    May 17, 2012

(51) Int. Cl.
*G01N 1/22* (2006.01)

(52) U.S. Cl.
USPC ..... 73/863.23; 73/53.01; 73/61.42; 73/61.71; 494/36

(58) Field of Classification Search
USPC ........... 73/53.01, 61.41, 61.42, 61.63, 61.71, 73/863.21, 863.23–863.25; 422/72; 494/36
See application file for complete search history.

(56) References Cited

U.S. PATENT DOCUMENTS

| | | | | |
|---|---|---|---|---|
| 3,440,864 A | * | 4/1969 | Blume | 73/61.53 |
| 4,253,953 A | * | 3/1981 | Libertini | 210/167.02 |
| 4,255,099 A | * | 3/1981 | Komori | 418/97 |
| 5,506,501 A | | 4/1996 | Fogel et al. | |
| 5,586,161 A | * | 12/1996 | Russell et al. | 378/45 |
| 5,804,366 A | * | 9/1998 | Hu et al. | 435/1.1 |
| 6,319,417 B1 | | 11/2001 | Rodibaugh | |
| 6,582,661 B1 | * | 6/2003 | Pardue et al. | 422/68.1 |
| 6,752,920 B2 | * | 6/2004 | Harris et al. | 210/107 |
| 7,107,824 B1 | * | 9/2006 | Shiff et al. | 73/61.43 |
| 7,175,771 B2 | * | 2/2007 | Bridges | 210/787 |
| 7,713,708 B2 | * | 5/2010 | Roback et al. | 435/7.1 |

FOREIGN PATENT DOCUMENTS

JP    2007-263786 A    10/2007

* cited by examiner

*Primary Examiner* — Hezron E Williams
*Assistant Examiner* — Hoang Nguyen
(74) *Attorney, Agent, or Firm* — Nath, Goldberg & Meyer; Jerald L. Meyer

(57) ABSTRACT

A method for wear analysis. The method includes introducing a lubricant sample into a tube. The lubricant sample includes debris, wear, or other particles of different sizes. The tube includes a number of filter patches, each of a predetermined pore size. The method further includes centrifuging the tube for displacing the lubricant sample, and the wear particles thereof, along a length of the tube. The filter patches impede passage of wear particles of a size larger than their pore size therethrough, thereby separating the wear particles according to the sizes of the wear particles. The tube is attached to a handler of a centrifuge for centrifugation by the centrifuge. Multiple tubes can be attached to multiple handlers of the centrifuge for simultaneous centrifugation by the centrifuge. Centrifugation tubes (or tubes) are also provided by the present disclosure.

25 Claims, 14 Drawing Sheets

APPARATUS AND METHOD FOR PARTICLE ANALYSIS

TECHNICAL FIELD

The present disclosure relates generally to apparatuses and methods for evaluating the particulate content of fluids. More specifically, the present disclosure relates to apparatuses and methods for measuring an amount of wear associated with a machine system or component. Several apparatuses and methods of the present disclosure incorporate the use of centrifugation.

BACKGROUND

Wear is an unavoidable occurrence in machine systems and components. The ability to measure wear is essential for implementing effective predictive maintenance programs, and for determining safety factors and performance ratings.

Generally, there are two options for measuring wear in machine systems and components. The first option is via interceptive or disruptive means whereby the machine system is disassembled and wearing surfaces of the machine system visually examined. Measuring wear via such interceptive means disrupts the overall operation of the machine system and can result in a loss of productivity and increased costs. The second option for measuring wear in machine systems and components is via non-interceptive techniques such as wear particle analysis, which is also known as lubricant analysis. In wear particle analysis, a lubricant sample, more specifically an oil sample, is taken from the machine system and tested separately.

Modern integrated and automated high-speed machine systems typically make any interval of down time non-productive and costly. Accordingly, non-interceptive techniques such as wear particle analysis are particularly useful for measuring wear of such systems. Common wear particle analysis techniques include spectroscopic analysis, ferrography, filter patch analysis, and magnetic chip detector (MCD) wear particle analysis.

Spectroscopic Analysis

In standard spectroscopic analysis, the lubricant sample is diluted and aspirated into an energy source which excites wear metals, or wear particles, within the lubricant sample such that the wear metals give off optical emissions at visible wavelengths. The optical emissions can be registered and analysed for determining size and quantity of the wear metals within the lubricant sample, and accordingly measuring the wear of the machine system. However, spectroscopic analysis typically requires the lubricant sample to be in solution. In addition, spectroscopic analysis methods are generally unable to accurately detect particles that are larger than 10 micrometers.

Ferrography

Ferrography is also commonly used for determining or measuring wear of machine systems. Typically, wear particles are magnetically precipitated from the lubricant sample and then microscopically examined. The determination of at least one of quantity, size, and type of wear particles within the lubricant sample provides an indication of the wear status of the machine system. Three major types of equipment used in ferrography are Direct-Reading (DR) Ferrograph, Analytical Ferrograph System, and Ferrogram Scanner. The equipment required for ferrography can be expensive, bulky, and complicated to operate.

Filter Patch Analysis

A known wear analysis tool is the 51WD Wear Debris Filter Patch Maker from Emerson Process Management. The 51WD Wear Debris Filter Patch Maker is designed to separate wear particles from used oil samples for viewing under a microscope. With the 51WD Wear Debris Filter Patch Maker, a vacuum pump is required for pulling a diluted used oil sample through a set of filter patches to separate wear particles within the oil sample based on sizes of the wear particles. There are several limitations associated with the 51WD Wear Debris Filter Patch Maker. Such limitations include a relatively low efficiency and a fixed minimum cost associated with the use of the 51WD Wear Debris Filter Patch Maker.

Magnetic Chip Detector (MCD) Wear Particle Analysis

A magnetic chip detector (MCD) is typically used for collecting wear particles, more specifically ferrous wear particles or debris, from lubricant (e.g., used oil) samples. MCD wear particle analysis involves collection of ferrous wear particles from the MCD, examination of the collected ferrous wear particles, and assimilation of information gathered during the examination to form an assessment of the wear condition of a machine system. Typically, large sized ferrous wear particles (i.e. particles larger than 100 microns) are collected from the MCD. The ferrous wear particles collected from the MCD can be examined or assessed using both quantitative analysis and qualitative analysis.

The increasing importance of machine system and component maintenance programs has resulted in a growing need for accurate, reliable, and cost-effective wear analysis apparatuses, tools, systems, and methods.

SUMMARY

In accordance with a first aspect of the present disclosure, there is disclosed a method for wear analysis including introducing a lubricant sample into a tube, the tube including a filter patch of a predetermined pore size. The method further includes centrifuging the tube for displacing the lubricant sample along a length of the tube and inhibiting passage of at least a portion of the lubricant sample through the filter patch, the at least a portion of the lubricant sample being larger than the predetermined pore size of the filter patch.

In accordance with a second aspect of the present disclosure, there is disclosed a method for wear analysis including introducing a first lubricant sample into a first tube, the first tube including a number of filter patches, each of the number of filter patches having a predetermined pore size. The method further includes introducing a second lubricant sample into a second tube, the second tube comprising a number of filter patches, each of the number of filter patches having a predetermined pore size, and centrifuging the first and second tubes simultaneously for displacing the first and second lubricant samples along a length of the first and second tubes respectively. At least one of the number of filter patches of the first and second tubes traps a portion of the first and second lubricant samples thereon respectively, the portion of the first and second lubricant sample trapped on the at least one of the number of filter patches being of a size larger than the predetermined pore size of the at least one of the number of filter patches.

In accordance with a third aspect of the present disclosure, there is disclosed a system for wear analysis including a first tube for accommodating a first lubricant sample comprising a plurality of wear particles, the first tube including a number of filter patches disposed therewithin, each of the number of filter patches having a predetermined pore size. The system further includes a centrifuge for centrifuging the first tube to displace the first lubricant sample along a length of the first tube. At least one of the number of filter patches inhibits passage of a portion of wear particles therethrough during displacement of the first lubricant sample along the length of the first tube, the portion of wear particles having a size larger than the predetermined pore size of the at least one of the number of filter patches.

In accordance with a fourth aspect of the present disclosure, there is disclosed a centrifugation tube. The tube includes a cylindrical receptacle having an opening and a plurality of filter patches, each of the plurality of filter patches being disposed at a predetermined position within the receptacle and having a predetermined pore size for trapping particles of a size larger than the predetermined pore size during centrifugation of the receptacle.

In accordance with a fifth aspect of the present disclosure, there is disclosed a centrifugation tube that includes a plurality of separable receptacle parts, which includes at least a first receptacle part and a second receptacle part. Each of the plurality of receptacle parts includes an opening and a fluid carrying channel. The least one filter patch is disposed between the first receptacle part and the second receptacle part and is transverse to the fluid carrying channel of each of the first receptacle part and the second receptacle part. The at least one filter patch has a predetermined pore size.

BRIEF DESCRIPTION OF THE DRAWINGS

Embodiments of the present disclosure are described herein with reference to the drawings, in which:

FIG. 2b shows a partial top view of the lid of FIG. 2a;

FIG. 3b shows a partial cross-sectional view of the first part of FIG. 3a;

FIG. 4b shows an alternative partial side view of the second part of FIG. 4a;

FIG. 5b shows an alternative partial side view of the third part of FIG. 5a;

FIG. 6b shows an alternative partial side view of the drain plug of FIG. 6a;

DETAILED DESCRIPTION

Figure 1:
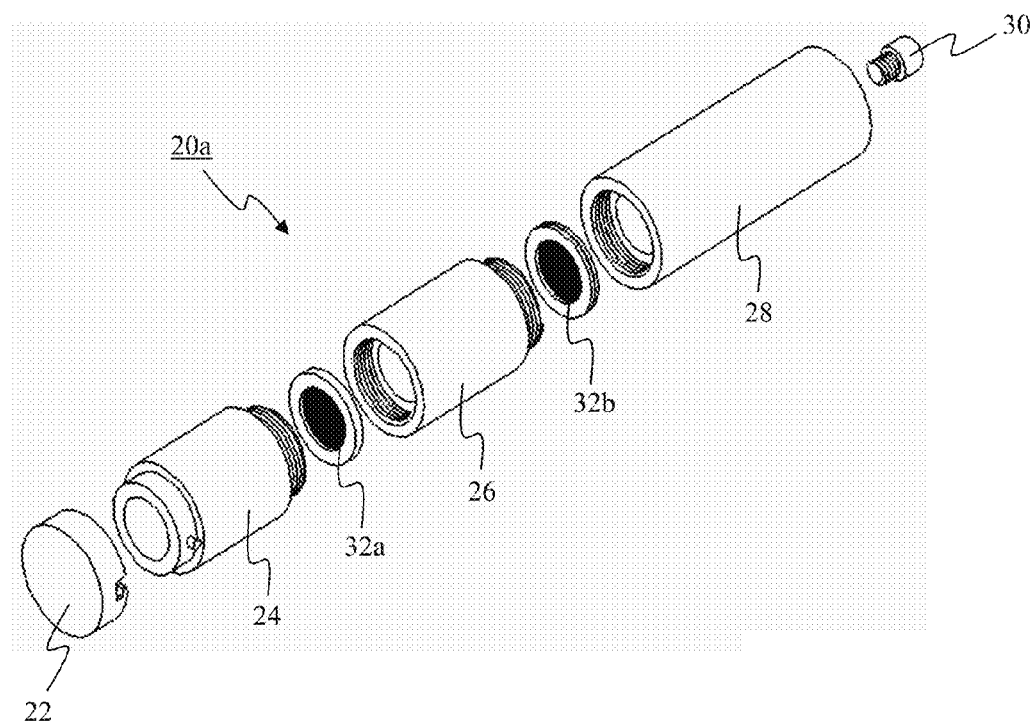
FIG. 1 shows a tube for wear analysis according to an embodiment of the present disclosure, the tube including two filter patches.

Wear particle analysis is a common method for measuring wear of machine systems and components. However, there are several limitations and disadvantages associated with existing wear particle analysis methods, systems, tools, and apparatuses. It is the object of the present disclosure to ameliorate at least one of these limitations and disadvantages.

Embodiments of the present disclosure are directed to systems, apparatuses, devices, methods, processes, procedures, and/or techniques for evaluating, estimating, characterizing, categorizing, or classifying a particulate content of liquids or liquid samples. More specifically, embodiments of the present disclosure are directed to systems, apparatuses, devices, methods, processes, procedures, and/or techniques for debris, wear, or other particle analysis. For simplicity and clarity of description, particulate matter may be generally referred to herein as wear particles. Various embodiments of the present disclosure are described hereinafter with reference to FIG. 1 to FIG. 12c, in which like elements are numbered with like reference numerals. Specific details of the described embodiments may be set forth to provide a thorough understanding of the described embodiments. However, it will be understood by a person skilled in the art that the embodiments of the present disclosure as described herein are not precluded from other applications where fundamental principles prevalent among the various embodiments of the present disclosure such as operational, functional or performance characteristics are required.

FIG. 1 shows a tube 20a according to an embodiment of the present disclosure. In general, the tube 20a is an elongated or cylindrical receptacle having at least one fluid carrying channel. In various embodiments of the present disclosure, the tube 20a includes a plurality of separable portions, segments, or parts, each of which has an opening and a fluid carrying channel. The tube 20a of FIG. 1 includes a lid 22, a first part 24 (also known as a top part), a second part 26 (also known as a middle part or a body part), a third part 28 (also known as a bottom part), a drain plug 30, and a number of filtration elements, filters, or filters patches 32a, 32b. The lid 22, the first part 24, the second part 26, the third part 28, the drain plug 30, and the number of the filter patches 32a, 32b can be coupled or assembled together to form the tube 20a. A given filter patch 32a, 32b is carried or positioned transverse to the tube's 20a fluid carrying channel.

In most embodiments of the present disclosure, the tube 20a is used for receiving, carrying, or containing a fluid or lubricant sample (not shown) therewithin. The lubricant sample can be, for example, a petroleum-based lubricant, a synthetic-based lubricant or synthetic lubricant, or a vegetable-based lubricant. In several embodiments of the present disclosure, the lubricant sample can be a used oil sample extracted or taken from a machine system or machine component (not shown). The used oil sample can be, for example, a used hydraulic oil sample, used gear oil sample, a used grease oil sample, or a used turbine oil sample. The lubricant sample includes wear particles of different sizes. Determination or estimation of the classification(s), characteristics and/or a quantity or density of wear particles, and more specifically in certain embodiments a relative quantity of wear particles of known size(s), facilitates measurement or evaluation of wear of the machine system or machine component.

The tube 20a according to the embodiment of the present disclosure as shown in FIG. 1 includes two filter patches 32a, 32b. Each filter patch 32a, 32b of the tube 20a has a predetermined pore size. In several embodiments of the present disclosure, the pore sizes of the filter patches 32a, 32b can be selected or determined as required. In various embodiments of the present disclosure, the pore sizes of the filter patches 32a, 32b are selected in relation to the type of lubricant sample to be analysed.

This is because different types of lubricant samples, more specifically different types of used oil samples (i.e., used hydraulic oil samples, used gear oil samples, used grease oil samples, or used turbine oil samples), can each contain wear particles of different sizes. Accordingly, to inhibit displacement or passage of a particular size wear particle through a particular filter patch, the pore size of that filter patch should be smaller than the size of the particular wear particle. For instance, used gear oil samples and used grease oil samples typically contain wear particles that are approximately 1000 micrometers in span, diameter, or width. In order to trap wear particles of approximately 1000 micrometers, the pore size of a filter patch should be smaller than approximately 1000 micrometers. In addition, used hydraulic oil samples typically contain wear particles of approximately five to 25 micrometers in size. Accordingly, to trap wear particles of approximately five to 25 micrometers, the pore size of a filter patch should correspondingly be smaller than approximately five to 25 micrometers.

For example, in some embodiments of the present disclosure, the pore sizes of the filter patches 32a, 32b are between approximately 800 and 1000 micrometers. Additionally or alternatively, in some embodiments of the present disclosure, the pore sizes of the filter patches 32a, 32b are smaller than 800 micrometers, for example, between approximately 2.5 to 25 micrometers.

In several embodiments of the present disclosure, the filter patches 32a, 32b are made substantially from plastic, or a plastic polymer. In other embodiments, one or more filter patches 32a, 32b can include a fine wire mesh configured for producing a predetermined pore size (also known as mesh size). The use of the fine wire mesh allows a user to heat the fine wire mesh of the filter patches 32a, 32b following a centrifugation process such as that described below to observe a response of wear particles trapped thereon to heat, for example, at a temperature in a range between approximately 150° C. and 350° C., and more specifically between about 200° C. and 300° C. In general, following a centrifugation process, one or more filter patches 32a, 32b can be subjected to a set of tests (e.g., thermal, chemical, or optical tests) to facilitate characterization of wear particles carried thereby.

As described above, the tube 20a according to the embodiment of the present disclosure as shown in FIG. 1 includes the lid 22, the first part 24, the second part 26, the third part 28, the drain plug 30, and the number of the filter patches 32a, 32b, which are coupled or assembled together to form the tube 20a.

Figure 2A:
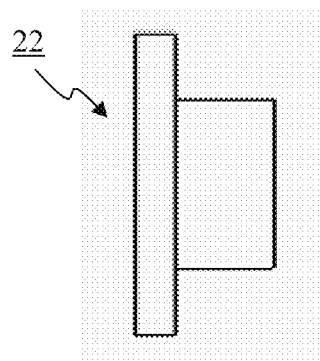
FIG. 2a shows a partial side view of a lid of the tube of FIG. 1.
Figure 2B:
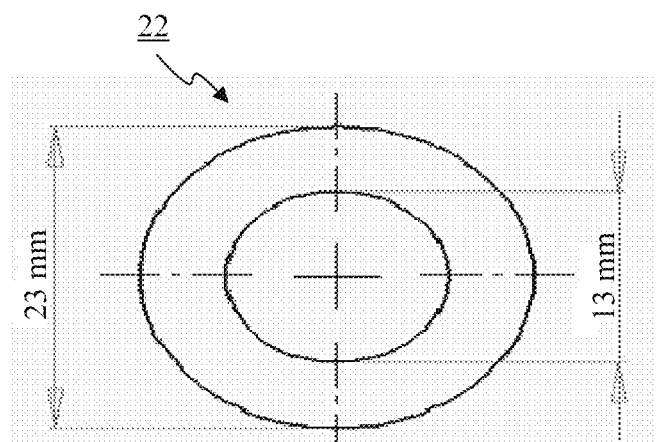
Figure 2C:
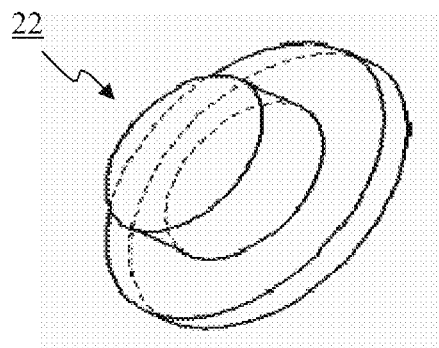
FIG. 2c shows a partial isometric view of the lid of FIGS. 2a and 2b.
Figure 3A:
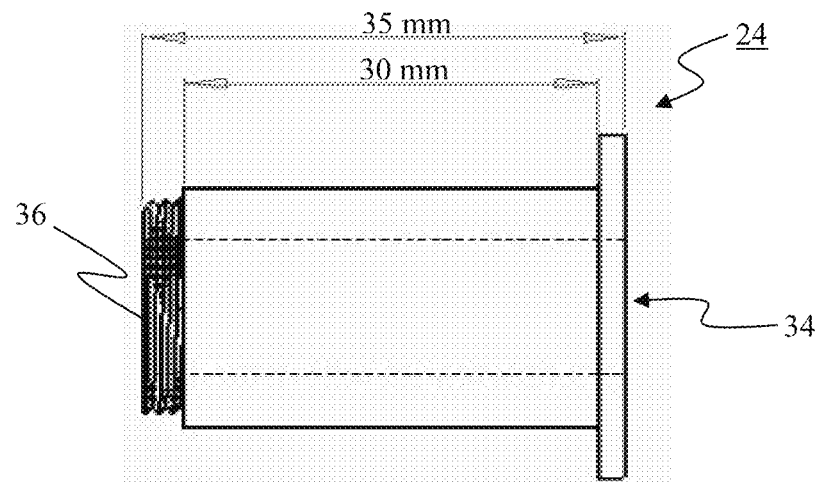
FIG. 3a shows a partial side view of a first part of the tube of FIG. 1.
Figure 3B:
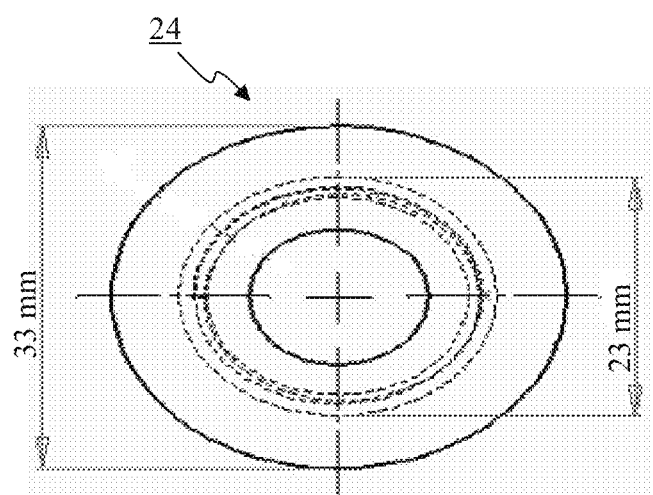
Figure 3C:
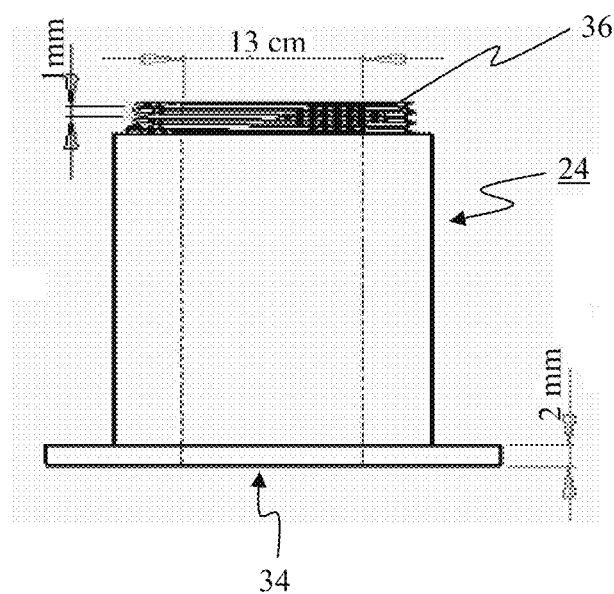
FIG. 3c shows an alternative partial side view of the first part of FIG. 3a and FIG. 3b.
Figure 3D:
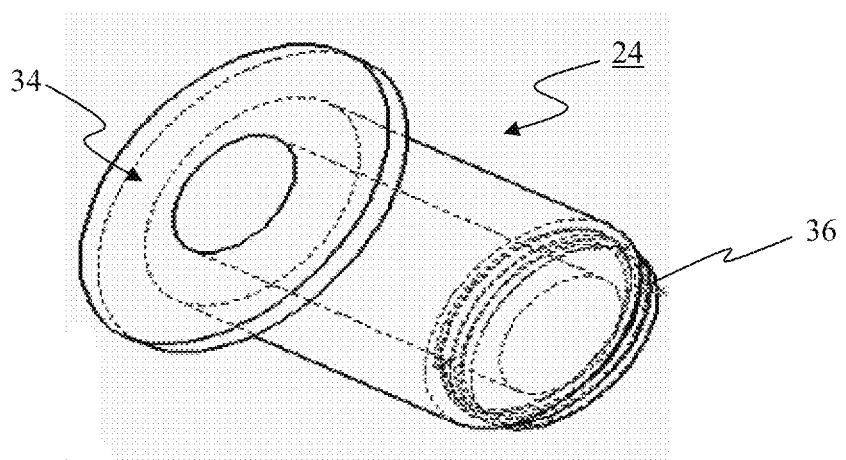
FIG. 3d shows a partial isometric view of the first part of FIG. 3a, FIG. 3b and FIG. 3c.
Figure 4A:
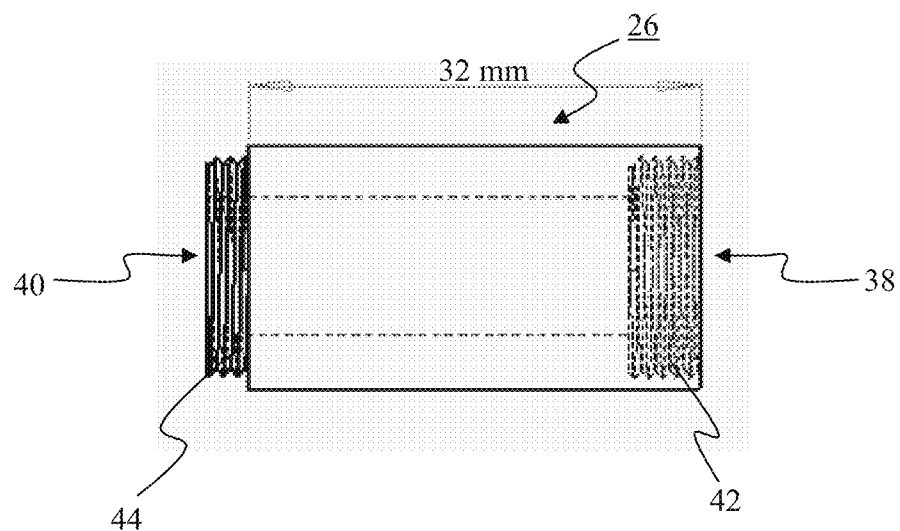
FIG. 4a shows a partial side view of a second part of the tube of FIG. 1.
Figure 4B:
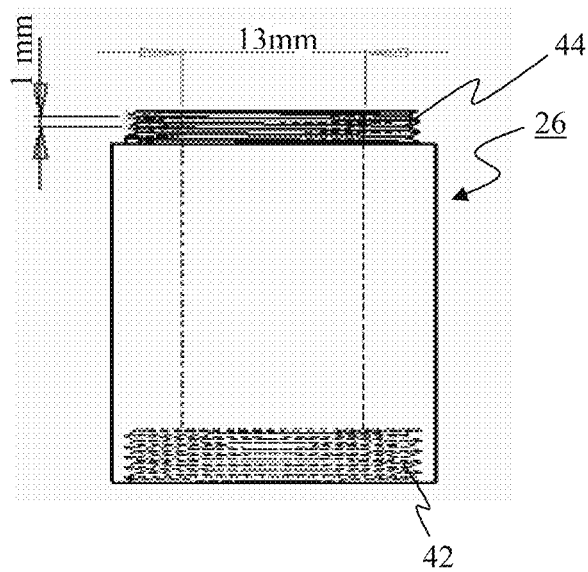
Figure 4C:
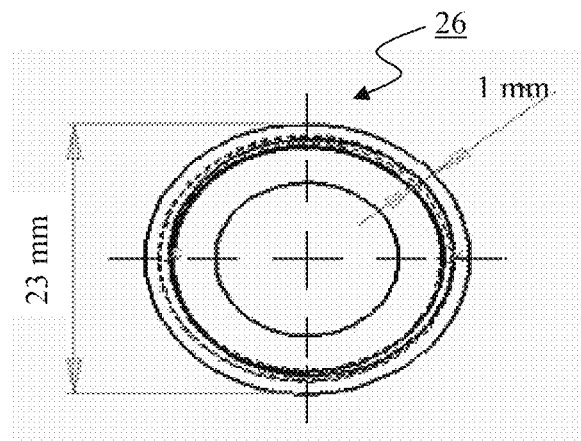
FIG. 4c shows a partial cross-sectional view of the second part of FIG. 4a and FIG. 4b.
Figure 4D:
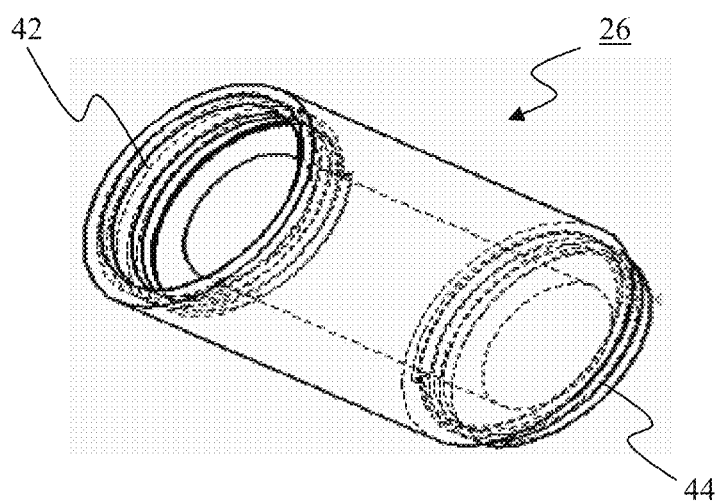
FIG. 4d shows a partial isometric view of the second part of FIG. 4a, FIG. 4b, and FIG. 4c.
Figure 5A:
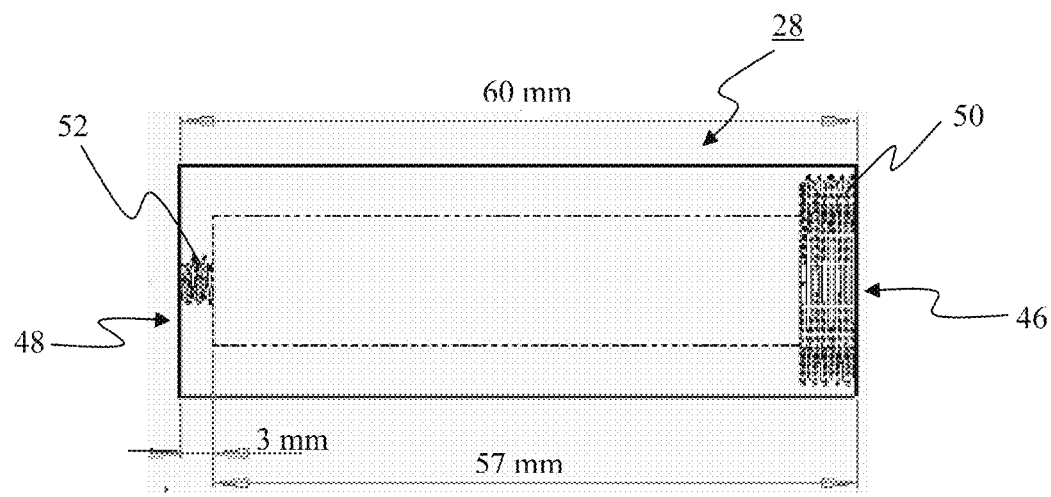
FIG. 5a shows a partial side view of a third part of the tube of FIG. 1.
Figure 5B:
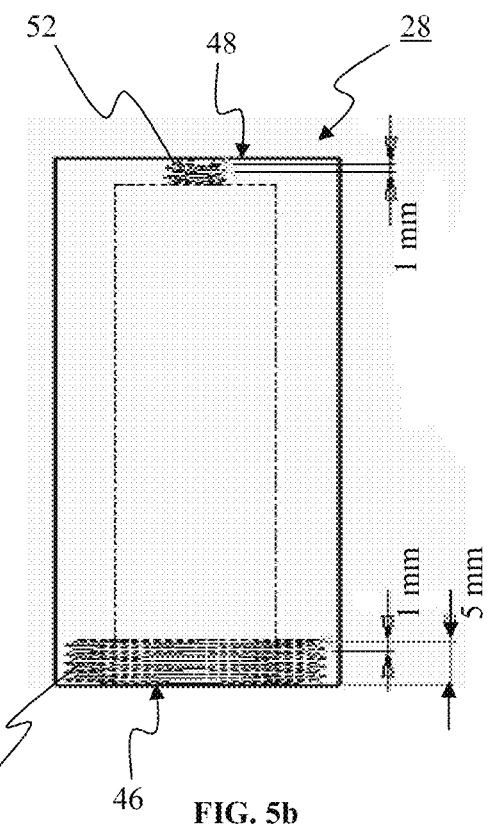
Figure 5C:
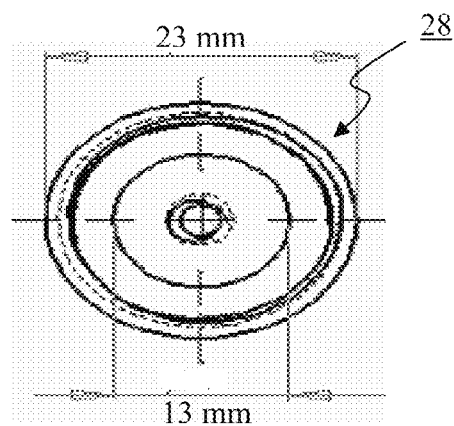
FIG. 5c shows a partial cross-sectional view of the third part of FIG. 5a and FIG. 5b.
Figure 5D:
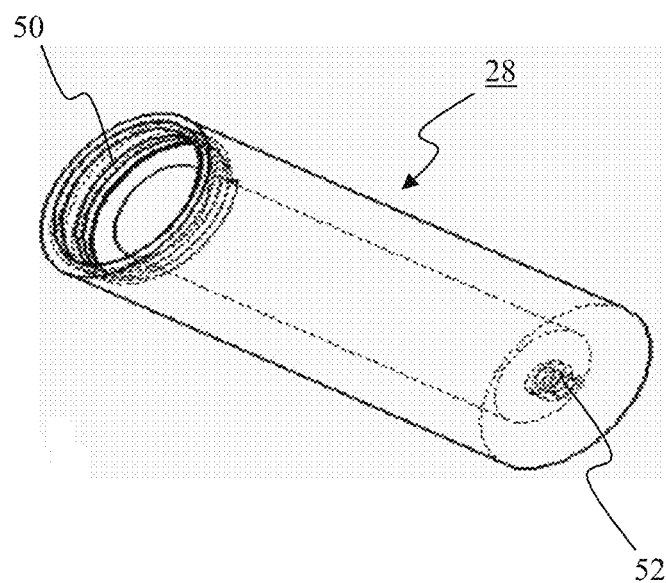
FIG. 5d shows a partial isometric view of the third part of FIG. 5a, FIG. 5b, and FIG. 5c.

FIG. 2a to 2c show the lid 22 according to an embodiment of the present disclosure. In most embodiments of the present disclosure, the lid 22 is shaped and dimensioned for fit coupling with the first part 24, which is shown in FIG. 3a to 3c. More specifically, the lid 22 is shaped and dimensioned for fit coupling to a receiving surface 34 of the first part 24. In most embodiments of the present disclosure, the first part 24 is a hollow cylindrical structure that is shaped and dimensioned for coupling to each of the lid 22 and the second part 26 of the tube 20a. The first part 24 of the tube 20a includes screw threads 36. In most embodiments of the present disclosure, the screw threads 36 of the first part 24 of the tube 20a are located distal to the receiving surface 34.

FIG. 4a to 4d show the second part 26 of the tube 20a. In most embodiments of the present disclosure, the second part 26 is a hollow cylindrical structure that is shaped and dimensioned for coupling to each of the first part 24 and the third part 28 of the tube 20a. The second part 26 of the tube 20a includes a first end 38 and a second end 40, which are located on opposite ends of the second part 26 of the tube 20a. The first end 38 of the second part 26 includes a first set of screw threads 42 that are shaped and dimensioned for receiving or coupling to the screw threads 36 of the first part 24. The second end 40 of the second part 26 includes a second set of screw threads 44.

Figure 6A:
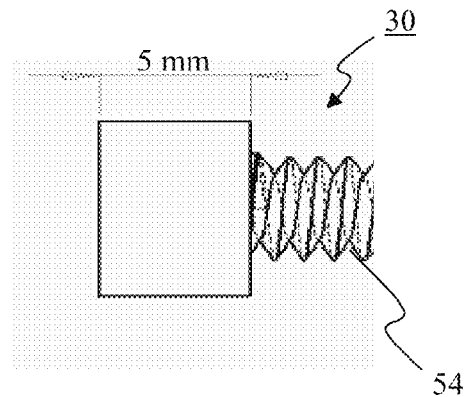
FIG. 6a shows a partial side view of a drain plug of the tube of FIG. 1.
Figure 6B:
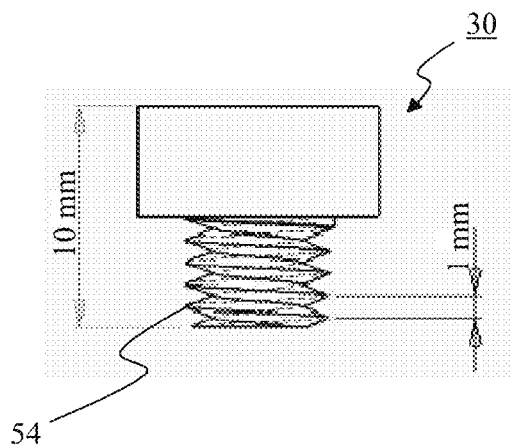
Figure 6C:
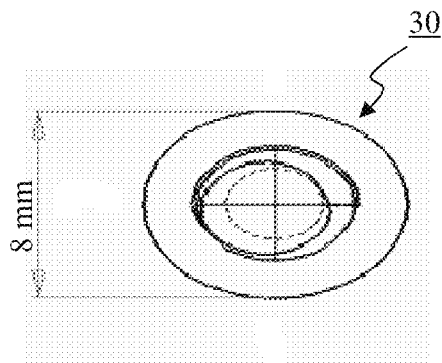
FIG. 6c shows a cross-sectional view of the drain plug of FIG. 6a and FIG. 6b.

FIG. 5a to 5d show the third part 28 of the tube 20a. In most embodiments of the present disclosure, the third part 28 is a hollow cylindrical structure that is shaped and dimensioned for coupling to each of the second part 26 and the drain plug 30. The third part 28 includes a first end 46 and a second end 48, which are located on opposite ends of the third part 28. The first end 46 includes a first set of screw threads 50 that are shaped and dimensioned for receiving or coupling to the second set of screw threads 44 of the second part 26 of the tube 20a. FIG. 6a to 6c show the drain plug 30 of the tube 20a. The drain plug 30 includes screw threads 54, which are shaped and dimensioned for coupling to the second set of screw threads 52 of the third part 28 of the tube 20a.

In most embodiments of the present disclosure, the filter patches 32a, 32b are assembled or secured within the tube 20a via mechanical means. In the embodiment of the present disclosure as shown in FIG. 1, the first filter patch 32a is assembled between first part 24 and the second part 26 of the tube 20a and the second filter patch 32b is assembled between the second part 26 and the third part 28 of the tube 20a. In several embodiments of the present disclosure, the filter patches 32a, 32b include screw threads (not shown) formed on the periphery thereof which facilitates mechanical coupling or assembly of the filter patches 32a, 32b to either of the first part 24, the second part 26, and the third part 28 of the tube 20a. In other embodiments, the filter patches 32a, 32b do not include screw threads, and may be carried by or positioned upon a seating or support portion of a tube part 24, 26, 28. Mechanical structures, gaskets, o-rings, or other types of sealing elements can be employed (e.g., as separate elements or as a portion of the filter patches 32a, 32b or a filter patch assembly) to facilitate fluid sealing within the tube 20a.

Figure 7:
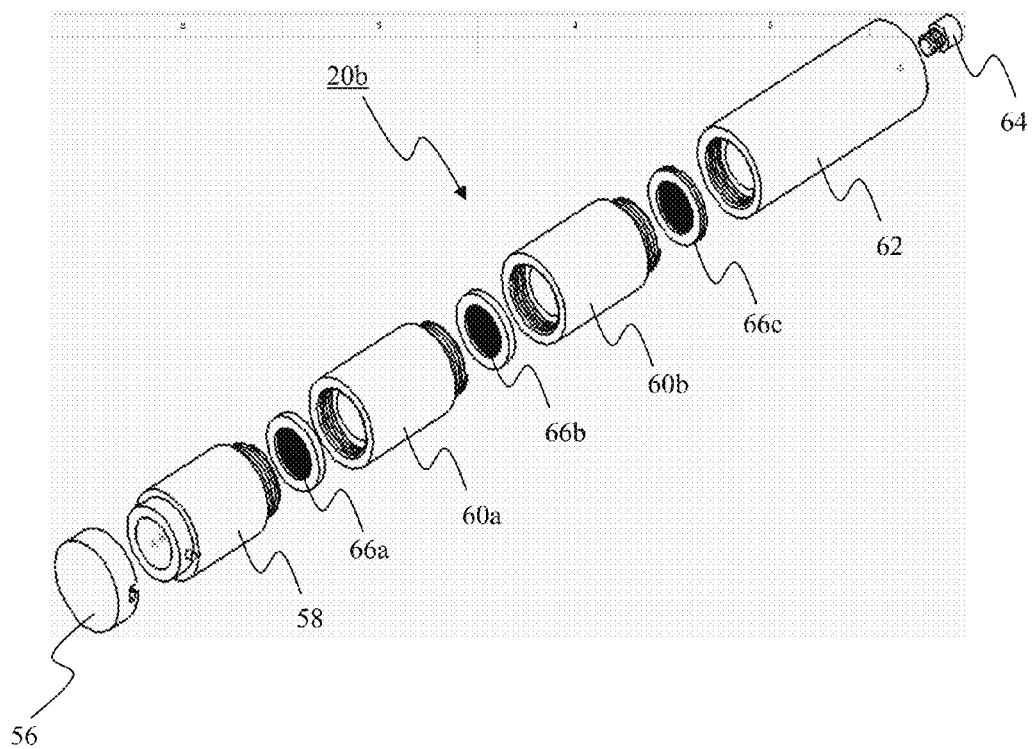
FIG. 7 shows a tube for wear analysis according to another embodiment of the present disclosure, the tube including three filter patches.

In the embodiment of the present disclosure shown in FIG. 1, the tube 20a includes two filter patches 32a, 32b. It will be understood by a person skilled in the art that tubes with different numbers of filter patches can be provided by other embodiments of the present disclosure. For example, tubes according to other embodiments of the present disclosure may include three, four, five, or more filter patches. FIG. 7 shows a tube 20*b* that includes three filter patches 66*a*, 66*b*, 66*c*. The tube 20*b* also includes a lid 56, a first part 58 (also known as a top part), two second parts 60*a*, 60*b* (also known as middle parts), a third part 62 (also known as a bottom part), and a drain plug 64. In most embodiments of the present disclosure, each of the lid 56, the first part 58, the two second parts 60*a*, 60*b*, the third part 62, and the drain plug 64 of the tube 20*b* has a similar construction, and function, to the lid 22, the first part 24, the second part 26, the third part 28, and the drain plug 30 of the tube 20*a*, correspondingly.

Figure 8A:
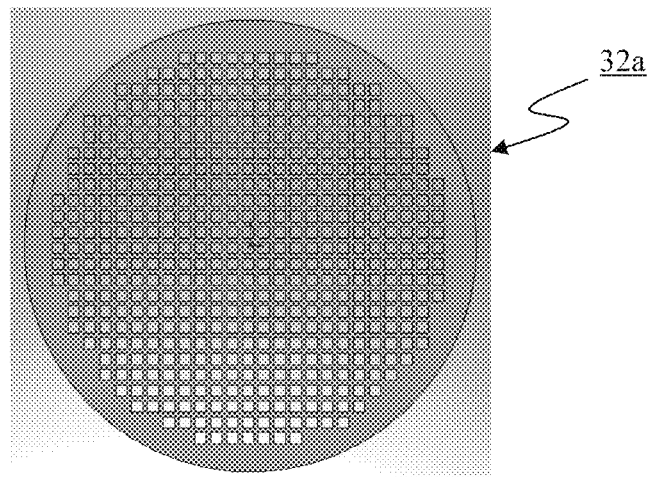
FIG. 8a shows a filter patch of a coarse pore size that is within the tube of FIG. 1 according to various embodiment of the present disclosure.
Figure 8B:
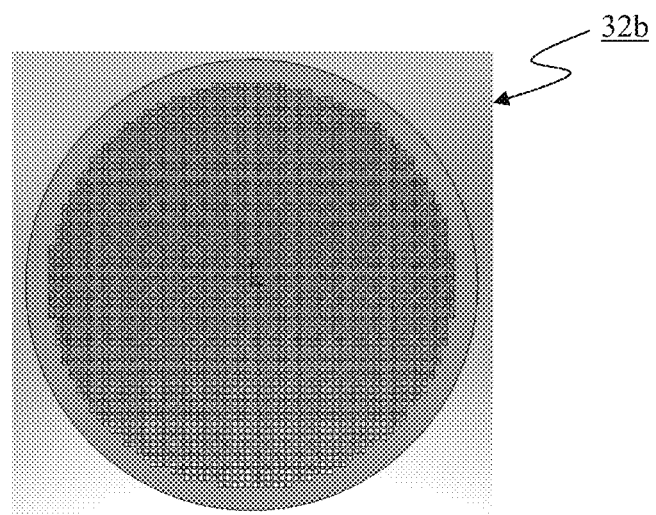
FIG. 8b shows a filter patch of a fine pore size that is within the tube of FIG. 1 according to various embodiments of the present disclosure.

In most embodiments of the present disclosure, the first filter patch 32*a* of the tube 20*a* has a coarse pore size as shown in FIG. 8*a*, and the second filter patch 32*b* of the tube 20*a* has a fine pore size as shown in FIG. 8*b*. In multiple embodiments of the present disclosure, the first filter patch 32*a* of the coarse pore size is positioned between the first part 24 and the second part 26, the second filter patch 32*b* of the fine pore size is positioned between the second part 26 and the third part 28 of the tube 20*a*. In most embodiments of the present disclosure, the filter patches 32*a*, 32*b*, 66*a*, 66*b*, 66*c* are positioned or sequentially ordered in the tubes 20*a*, 20*b* in accordance with their pore sizes, such that a coarsest pore size filter patch resides closest to the lids 22, 56 of the tubes 20*a*, 20*b* and filter patches 32*a*, 32*b*, 66*a*, 66*b*, 66*c* having progressively finer pore sizes reside successively further from the lids 22, 56 of the tubes 20*a*, 20*b*.

In most embodiments of the present disclosure, the position of each filter patch 32*a*, 32*b*, 66*a*, 66*b*, 66*c* relative to another filter patch 32*a*, 32*b*, 66*a*, 66*b*, 66*c* within either of the tubes 20*a*, 20*b* is fixed during centrifugation of the tubes 20*a*, 20*b*. In several embodiments of the present disclosure, the spacing between the filter patches 32*a*, 32*b*, 66*a*, 66*b*, 66*c* within the tubes 20*a*, 20*b* is fixed, i.e., remains unchanged, during centrifugation of the tubes 20*a*, 20*b*.

It will be understood that in other embodiments of the present disclosure, one or more filter patches within tubes can initially reside at a given location or region within the tubes, and the positions of the filter patches with respect to the tubes and/or each other may be adjusted or varied before centrifugation (e.g., manually); during centrifugation (e.g., as a result of centrifugal force acting upon and separating the filter patches); or after centrifugation. In several embodiments of the present disclosure, a filter patch assembly can include multiple filter patches that can be drawn away from each other along an axis that is normal to a filter patch filtration surface, in response to a centrifugal force or other forces (e.g., gravity).

Figure 9:
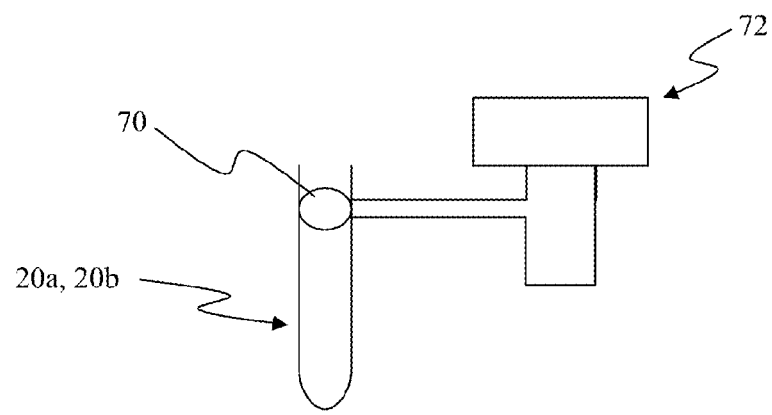
FIG. 9 shows the tube of FIG. 1 or the tube of FIG. 7 attached to a handler of a centrifuge according to an embodiment of the present disclosure.
Figure 10:
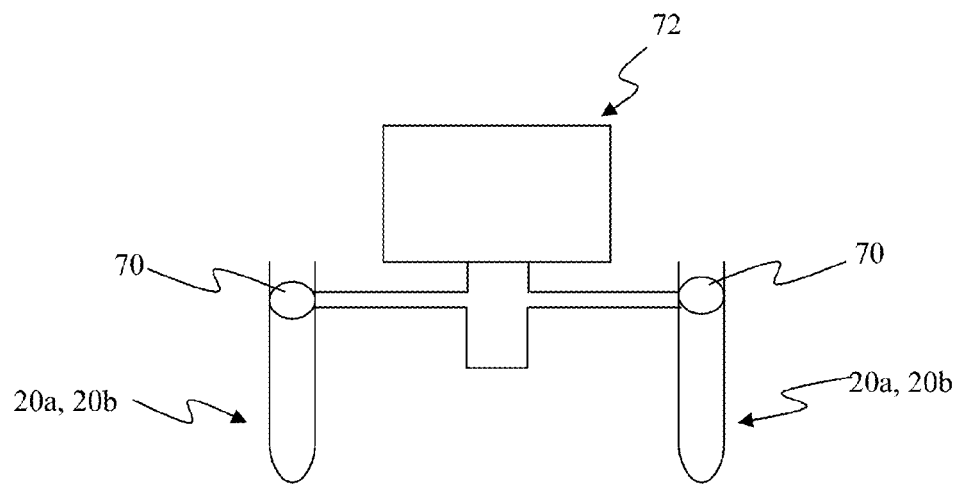
FIG. 10 shows multiple tubes of FIG. 1 or multiple tubes of FIG. 7 attached to multiple handlers of the centrifuge according to an embodiment of the present disclosure.

FIG. 9 shows the tube 20*a*, 20*b* attached or coupled to a handler 70 of a centrifuge 72 (also known as a centrifuge unit, centrifugation apparatus, a rotatory displacer, or a spinner) according to an embodiment of the disclosure. In several embodiments, the centrifuge 72 can be portable and/or hand held. In various embodiments of the present disclosure, the centrifuge 72 includes multiple handlers 70. FIG. 10 shows multiple tubes 20*a*, 20*b* attached to multiple handlers 70 of the centrifuge 72 according to several embodiments of the present disclosure. In some embodiments of the present disclosure, the centrifuge 72 includes four handlers 70, each handler 70 extending from a central motor assembly at an approximate 90-degree angle from each other (such a centrifuge can be referred to as a four-fixed wing centrifuge). In other embodiments, the centrifuge 72 can include an alternate number of handlers 70 extending from a central motor assembly at predetermined angles from each other.

In most embodiments of the present disclosure, the centrifuge 72 is operable for spinning, or centrifuging, the tube 20*a*, 20*b* about an axis of rotation of the centrifuge 72 (also known as a central axis). In several embodiments of the present disclosure, a speed of spin, or speed of centrifugation, of the tube 20*a*, 20*b* about the axis of rotation can be varied as required by a user of the centrifuge 72. In some embodiments of the present disclosure, the centrifuge 72 is programmed or programmable for setting a predetermined speed of spin, or speed of centrifugation, of the tube 20*a*, 20*b* about the axis of rotation.

In some embodiments of the present disclosure, the centrifuge 72 is operated for centrifuging the tube 20*a*, 20*b* at a speed of centrifugation between 750 RPM (revolutions per minute) and 1500 RPM for between 0.5 and two minutes. The speed and/or time of centrifugation can be varied according to a type of lubricant sample (i.e., type of oil sample) introduced into the tube 20*a*, 20*b*. In addition, the speed and/or time of centrifugation can be varied according viscosity of the lubricant sample introduced into the tube 20*a*, 20*b*. For example, a heavy gear oil sample (without dilution) will typically require centrifugation of between 1000 RPM and 1500 RPM for between one and two minutes. A hydraulic oil sample will typically require centrifugation of between 750 RPM and 1000 RPM for less than one minute.

In many embodiments of the present disclosure, the centrifugation of the tube 20*a*, 20*b* produces a centrifugal force along a length or longitudinal axis of the tube 20*a*, 20*b*, thereby displacing the lubricant sample, and the wear particles within the lubricant sample, a distance along the length of the tube 20*a*, 20*b*. In various embodiments, the centrifugation of the tube 20*a*, 20*b* pulls or displaces at least a portion of the wear particles through one or more of the filter patches 32*a*, 32*b*, 66*a*, 66*b*, 66*c*. It is understood that a filter patch having a pore size smaller than the size of a particular wear particle will impede passage of that particular wear particle through or across that filter patch. Accordingly, wear particles of a size larger than the pore size of a particular filter patch are trapped by that filter patch. In many embodiments of the present disclosure, centrifugation of the tube 20*a*, 20*b* draws a lubricant sample along at least part of the length of the tube 20*a*, 20*b* and facilitates separation of the wear particles from the rest of the lubricant sample, and from each other, based on the sizes of the wear particles.

As above described, in many embodiments of the present disclosure, the centrifuge 72 includes multiple handlers 70. Accordingly, in many embodiments, multiple tubes 20*a*, 20*b* can be simultaneously attached or coupled to the centrifuge 72. The ability to attach multiple tubes 20*a*, 20*b* to the centrifuge 72 enables the simultaneous centrifugation of multiple tubes 20*a*, 20*b*, and therefore a simultaneous separation of the wear particles within multiple lubricant samples based on wear particle size(s). This increases the efficiency of wear particle analysis.

Figure 11:
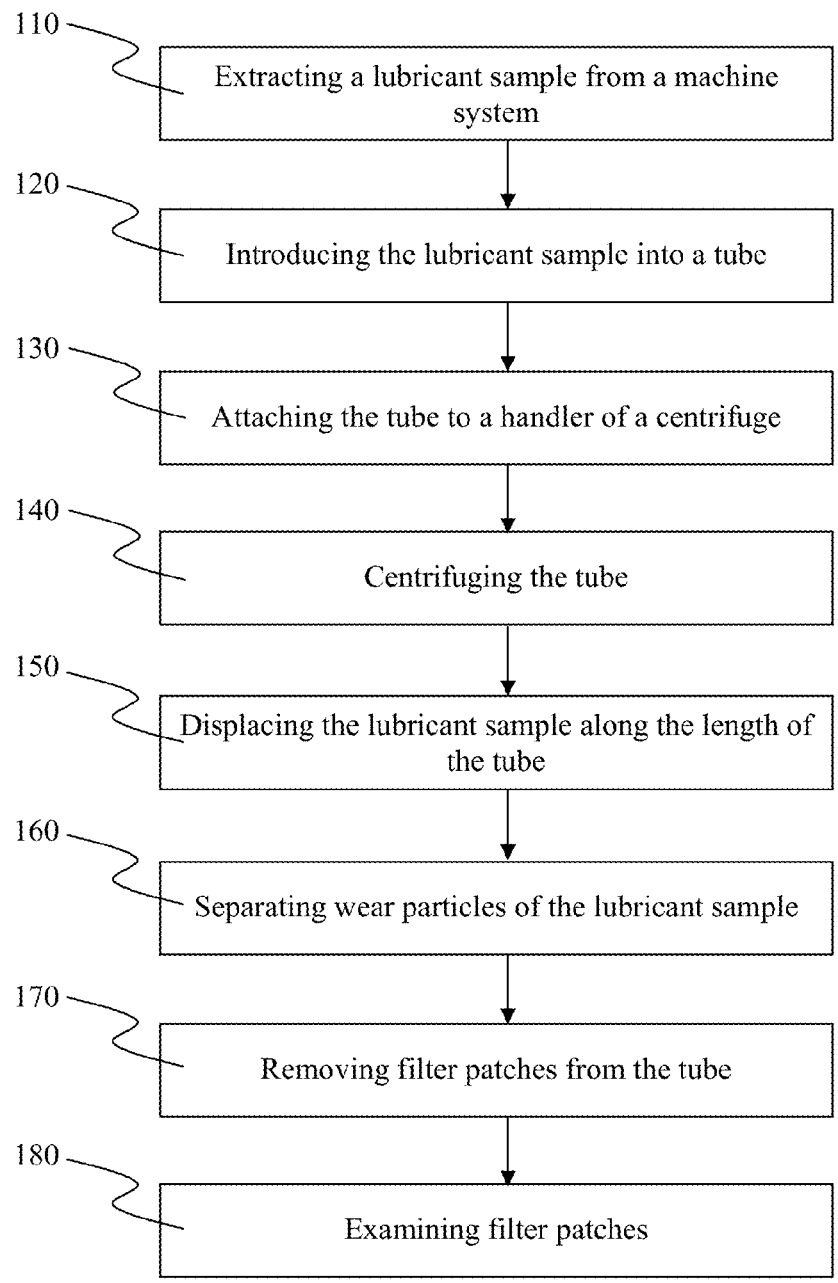
FIG. 11 is a flow chart of steps of a wear analysis process as according to an embodiment of the present disclosure.

FIG. 11 is a flow chart of a wear analysis process 100 according to an embodiment of the present disclosure.

In a first process portion 110 of the process 100, a lubricant sample is taken or extracted from a machine system or machine component. Conventional extraction or sampling techniques can be employed for extracting the lubricant sample from the machine system. The volume of lubricant sample extracted from the machine system is variable and can be varied depending on a number of factors including, but not limited to, a type of lubricant sample and/or a partial tube volume corresponding to a distance between the lid 22, 56 and a filter patch 32*a*, 32*b*, 66*a*, 66*b*, 66*c* that resides closest to the lid 22, 56 of the tube 20*a*, 20*b*. In several embodiments of the present disclosure, the volume of the lubricant sample extracted from the machine system is approximately ten to twenty milliliters. In other embodiments, the volume of the lubricant sample extracted from the machine system is more than twenty milliliters.

In a second process portion 120, the lubricant sample is introduced into the assembled tube 20a, 20b (e.g., into a first or upper chamber that is formed by the tube's 20a, 20b first part 24, 58). The size, dimensions, shape, lengths, diameters, and material of the tube 20a, 20b can be varied as required. The volume of the tube 20a, 20b can be varied depending on any one or more of volume, type, and viscosity of the lubricant sample to be analysed.

In several embodiments of the present disclosure, the tube 20a, 20b is made at least partially of a plastic polymer, and is between approximately twenty and thirty millimeters in external diameter, between approximately ten and fifteen millimeters in internal diameter, and between approximately five and fifteen centimeters in length. In various embodiments of the present disclosure, the tube 20a, 20b has an external diameter of approximately twenty-three millimeters and an internal diameter of approximately thirteen millimeters. In some embodiments of the present disclosure, the length of the first part 24, 58 is between approximately thirty and thirty-five millimeters, the length of the second part 26, 60 is between approximately thirty and thirty-five millimeters, and the length of the third part 28, 62 is between approximately fifty-five and sixty millimeters.

As described above, the tube 20a, 20b includes a number of filter patches 32a, 32b, 66a, 66b, 66c. Each of the number of filter patches 32a, 32b, 66a, 66b, 66c is of a predetermined pore size for impeding the passage of wear particles of a larger size than the predetermined pore size through or across the corresponding filter patch 32a, 32b, 66a, 66b, 66c. In several embodiments, the filter patches 32a, 32b, 66a, 66b, 66c are disposable filter patches that can be introduced (i.e., coupled to the first part 24, 58, the second part 26, 60, or the third part 28, 62) and removed from the tube 20a, 20b as needed or desired. As described above, the filter patches 32a, 32b, 66a, 66b, 66c can be inserted into the tube 20a, 20b (i.e., coupled to the first part 24, 58, the second part 26, 60, or the third part 28, 62) via mechanical means or methods, e.g. by means of screw threads. The filter patches 32a, 32b, 66a, 66b, 66c can also be removed or extracted from the tube 20a, 20b by mechanical means, tools, devices, or methods. In many embodiments of the present disclosure, the filter patches 32a, 32b, 66a, 66b, 66c are introduced into the tube 20a, 20b prior to the second process portion 120.

In many embodiments of the present disclosure, the filter patches 32a, 32b, 66a, 66b, 66c are each positioned at a predetermined position relative each other within the tube 20a, 20b. As described above, a filter patch 32a, 32b, 66a, 66b, 66c with a coarsest or largest pore size is positioned near the opening of the tube in comparison with a filter patch 32a, 32b, 66a, 66b, 66c having a finer pore size. In several embodiments, the filter patches 32a, 32b, 66a, 66b, 66c are each positioned at a fixed depth within the tube 20a, 20b. In addition, in several embodiments, the filter patches 32a, 32b, 66a, 66b, 66c are positioned at a fixed spacing relative each other, and are held immobile during centrifugation of the tube 20a, 20b. In other embodiments of the present disclosure, certain filter patches introduced within the tube do not have a fixed position in relation to the tube, and can be displaced (e.g., along the tube's length) at least one of before, during, and after centrifugation of the tube.

In a third process portion 130, the tube 20a, 20b is attached to, coupled to, fitted with, or placed into the handler 70 of the centrifuge 72. In various embodiments of the present disclosure, the centrifuge 72 is relatively cheap, portable, and easy to operate. As described above, in many embodiments of the present disclosure, the centrifuge 72 has multiple handlers 70, each handler 70 for handling, carrying, or coupling to one tube 20a, 20b. Accordingly, in many embodiments of the present disclosure, multiple tubes 20a, 20b can be attached to, coupled to, fitted with, or placed into, the multiple handlers 70 of the centrifuge 72 (e.g., in a sequential, simultaneous or generally simultaneous manner).

In a fourth process portion 140, the tube 20a, 20b is centrifuged. During centrifugation, at least a portion of the lubricant sample (e.g., particulate matter carried by the lubricant sample) is inhibited from passing through one or more filter patches 32a, 32b, 66a, 66b, 66c. In multiple embodiments of the present disclosure, one or more speeds of centrifugation of the tube 20a, 20b and/or a centrifugation time can be determined and adjusted as required by the user. For example, the speed of centrifugation can be determined according to any one or more of type, viscosity, and volume of lubricant sample in the tube 20a, 20b. In some embodiments of the present disclosure, the speed of centrifugation is between approximately 750 PRM to 1500 RPM for between approximately 0.5 to two minutes.

Figure 12A:
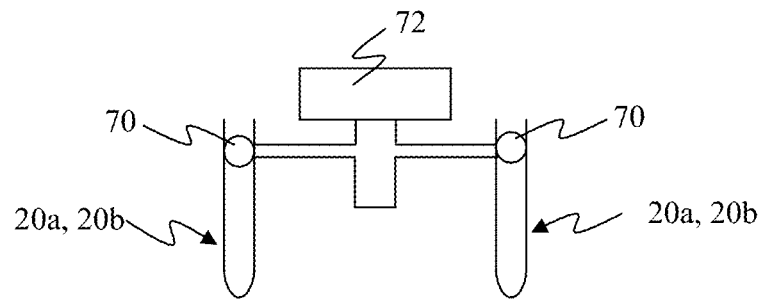
FIG. 12a to FIG. 12c show centrifugation of the tube of FIG. 1 or the tube of FIG. 7 performed in accordance with the wear analysis process of FIG. 11.
Figure 12B:
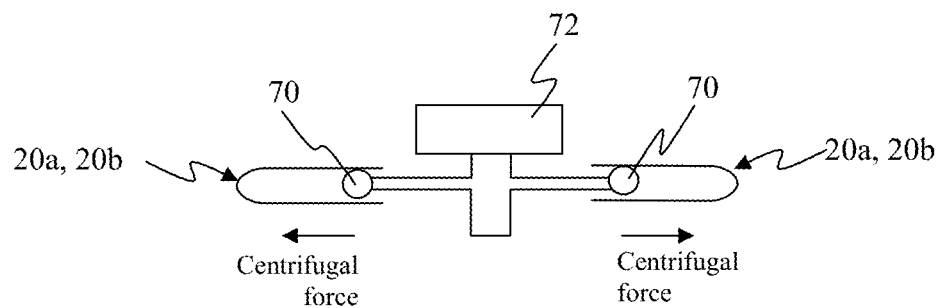
Figure 12C:
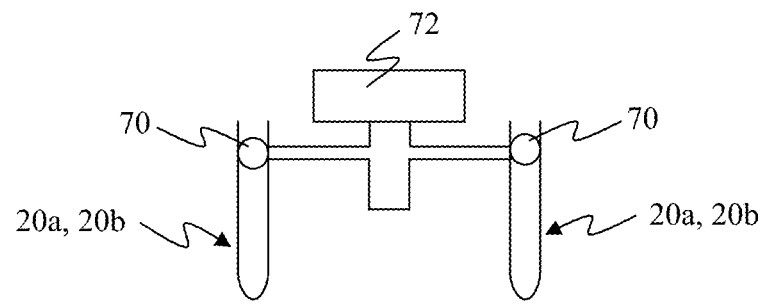

FIG. 12a to 12c show the centrifugation of two tubes 20a, 20b. Prior to and before centrifugation as shown in FIG. 12a and 12c, the tubes 20a, 20b can be positioned such that the length, or longitudinal axis, of the tubes 20a, 20b is parallel the axis of rotation, or axis of centrifugation, of the centrifuge 72. As seen in FIG. 12b, the centrifugation of the tubes 20a, 20b causes the tubes 20a, 20b to reorient. In some embodiments of the present disclosure, as a result of reaching a final or maximal speed of centrifugation, the tubes 20a, 20b reorient such that the lengths, or longitudinal axes of the tubes 20a, 20b, become substantially perpendicular the axis of rotation, or axis of centrifugation, of the centrifuge 72.

Centrifugation of the tubes 20a, 20b produces a centrifugal force along the length, or longitudinal axis, of the tubes 20a, 20b for displacing the lubricant sample along the lengths of the tubes 20a, 20b in a fifth process portion 150. Increasing the speed of centrifugation increases an amount of centrifugal force exerted on the lubricant sample, and on the wear particles of the lubricant sample. During centrifugation, the wear particles are displaced or drawn along the lengths of the tube tubes 20a, 20b, away from the tube's 20a, 20b lid 22, 56 and toward one or more filter patches 32a, 32b, 66a, 66b, 66c. Displacement of the wear particles along the lengths of the tubes 20a, 20b draws at least a portion of the lubricant sample and/or wear particles to, across, or through at least one filter patch 32a, 32b, 66a, 66b, 66c within the tubes 20a, 20b.

In many embodiments of the present disclosure, the wear particles are separated according to their sizes in a sixth process portion 160 as they are displaced along the length of the tube 20a, 20b. As above described, in some embodiments of the present disclosure, the filter patches 32a, 32b, 66a, 66b, 66c are each positioned at fixed depths (i.e., at a fixed spacing relative each other) within the tube 20a, 20b. Accordingly, the wear particles are separated based on their sizes as they are drawn across the filter patches 32a, 32b, 66a, 66b, 66c along the length of the tube 20a, 20b. Wear particles of a size larger than the pore size of a particular filter patch 32a, 32b, 66a, 66b, 66c will be trapped thereby, and wear particles of a size smaller than the pore size of a particular filter patch 32a, 32b, 66a, 66b, 66c will be able to pass therethrough.

In other embodiments of the present disclosure, one or more filter patches may not be positioned at fixed depths, and may not be held immobile, within the tubes. In such embodiments, the filter patches separate from each other in the sixth process portion 160 as the wear particles sediment after centrifugation of the tube. The separation of the filter patches is based on the pore sizes thereof, and accordingly, the sizes of the wear particles trapped thereby.

In a seventh process portion 170, the filter patches 32a, 32b, 66a, 66b, 66c are removed from the tube 20a, 20b. In association with the seventh process portion 170, the drain plug 30, 64 may be removed from the tube 20a, 20b to facilitate fluid drainage from the tube 20a, 20b. In several embodiments of the present disclosure, removal of the filter patches 32a, 32b, 66a, 66b, 66c is done via mechanical means, and is fast and cost-effective. In an eighth process portion 180, the filter patches 32a, 32b, 66a, 66b, 66c are examined, inspected, or tested (e.g., on an individual basis) for determining at least one of quantity, size, morphology, and type of wear particles trapped thereby. In multiple embodiments of the present disclosure, an optical apparatus is used for examining the filter patches 32a, 32b, 66a, 66b, 66c, more specifically the wear particles carried or trapped by or on the filter patches 32a, 32b, 66a, 66b, 66c. In various embodiments, the examination of the wear particles on the filter patches 32a, 32b, 66a, 66b, 66c is done via microscopy using an optical lens or microscope.

In many embodiments of the present disclosure, the ability to determine at least one of a type, size, and quantity or density of wear particles found within the lubricant sample enables the user to estimate or obtain data as to wear (i.e. wear status) of the machine system from which the lubricant sample was extracted. It will be understood that in embodiments of the present disclosure involving multiple tubes 20a, 20b, each coupled to one of the multiple handlers 70 of the centrifuge 72, particular process portions 110-180 can be performed simultaneously for multiple lubricant samples. Accordingly, the process 100 can be faster and more cost-effective than other techniques for wear analysis that are only capable of processing or analyzing individual lubricant samples one at a time. In addition, in several embodiments of the present disclosure, the centrifuge 72 is portable and easy to use, and therefore is suitable for on-site machine system or component wear measurement or evaluation. Accordingly, the process 100 according to multiple embodiments of the present disclosure can be versatile, convenient, fast, and cost-efficient.

It will be understood that particular embodiments of the present disclosure can be used for evaluating the particulate content of other liquid state samples. For example, various embodiments of the present disclosure can be used for determining at least one of size, morphology, and type of particles found in a liquid or liquid sample.

In the foregoing description, embodiments of the present disclosure are described with reference to the figures. Numerous changes and modifications can be made to the described embodiments of the present disclosure without departing from the scope or spirit of the present disclosure. The scope of the disclosure as well as the scope of the following claims is not limited to embodiments described herein.

The invention claimed is:

1. A method for wear analysis comprising:
   introducing a lubricant sample extracted from a machine and carrying suspended particles associated with machine wear into an elongate receptacle, wherein the receptacle comprises:
      a plurality of tubes pairwise detachably fastened to each other in an end-to-end fashion to jointly define a continuous channel within the receptacle, wherein an uppermost tube is configured to receive the lubricant sample; and
      a plurality of filter patches, each filter patch within the plurality of filter patches disposed between pairwise fastened tubes and each filter patch within the plurality of filter patches having a predetermined pore size;
   centrifuging the receptacle for displacing the lubricant sample along a length of the channel; and
   inhibiting passage of at least a portion of the suspended particles through the plurality of filter patches,
   wherein the at least a portion of the suspended particles includes particles having sizes larger than the predetermined pore size of each filter patch within the plurality of filter patches, and
   wherein pairwise fastened tubes are separable for removing or replacing the filter patch disposed therebetween.

2. The method as in claim 1, wherein the number of filter patches in the plurality of filter patches is adjustable by regulating the number of pairwise fastened tubes.

3. The method as in claim 1, wherein pairwise fastened tubes are fastened by way of a threaded-fastening mechanism.

4. The method as in claim 1, wherein a bottom-most tube includes a base sealed with a drain plug.

5. The method as in claim 1, wherein the predetermined pore size of each filter patch within the plurality of filter patches is between 2.5 and 25 micrometers.

6. The method as in claim 1, wherein the predetermined pore size of each filter patch within the plurality of filter patches is between 800 and 1200 micrometers.

7. The method as in claim 1, further comprising:
   removing at least one filter patch;
   carrying particles from the lubricant sample trapped thereon from the receptacle; and
   examining the filter patch for determining at least one of quantity and morphology of particles trapped thereon,
   wherein the determination of the at least one of quantity and morphology of particles trapped on the filter patch facilitates measurement of wear of the machine system.

8. A method for wear analysis comprising:
   introducing a plurality of machine lubricant samples, each of which carries suspended particles associated machine wear, into a corresponding plurality of elongate receptacles, each receptacle within the plurality of receptacles comprising:
      a plurality of tubes pairwise detachably fastened to each other in an end-to-end fashion to jointly define a continuous channel within the receptacle, wherein an uppermost tube is configured to receive the lubricant sample; and
      a plurality of filter patches, each filter patch within the plurality of filter patches disposed between pairwise fastened tubes and each filter patch within the plurality of filter patches having a predetermined pore size;
   centrifuging the plurality of receptacles simultaneously for displacing the lubricant sample within each receptacle along a length of the channel of each receptacle,
   trapping lubricant sample particles on at least one filter patch within the plurality of filter patches of each receptacle;
   removing the plurality of filter patches from each receptacle by way of detaching pairwise fastened tubes from each other; and
   subjecting at least one filter patch removed from each receptacle and upon which lubricant sample particles are trapped to a set of thermal, optical, or chemical tests to characterize the lubricant sample particles trapped thereby.

9. The method as in claim 1, wherein a filter patch positioned closest to the uppermost tube has a larger pore size relative to each filter patch positioned further away from the uppermost tube.

10. A system for wear analysis comprising:
a plurality of tubes pairwise detachably fastened to each other in an end-to-end fashion to jointly define an elongate receptacle having a continuous channel therewithin, wherein an uppermost tube of the plurality of tubes is configured to receive a lubricant sample which is extracted from a machine and which carries suspended particles associated with machine wear; and
a plurality filter patches carried by the receptacle, wherein each filter patch within the plurality of filter patches is disposed between pairwise fastened tubes for retaining at least portion of the suspended particles upon being subjected to centrifugal force,
wherein pairwise fastened tubes are separable for removing or replacing a filter patch disposed therebetween.

11. The system as in claim 10, wherein the number of filter patches within the plurality of filter patches is adjustable by regulating the number of pairwise fastened tubes.

12. The system as in claim 10, wherein pairwise fastened tubes are fastened by way of a threaded fastening mechanism.

13. The system as in claim 10, wherein a filter patch positioned closest to the uppermost tube has larger pore size relative to each filter patch positioned further away from the uppermost tube.

14. The system as in claim 10, wherein each filter patch within the plurality of filter patches has a pore size between 2.5 and 25 micrometers.

15. The system as in claim 10, wherein each filter patch within the plurality of filter patches has a pore size between 800 and 1200 micrometers.

16. The system as in claim 10, further comprising an optical apparatus for examining at least one of the of filter patches within the plurality of filter patches to determine quantity, size, and/or morphology of the portion of wear particles trapped thereon.

17. The apparatus of claim 10, further comprising a centrifuge for centrifuging the receptacle to displace the lubricant sample along a length of the channel.

18. A system for wear analysis comprising:
a plurality of receptacles, each receptacle comprising:
a plurality of tubes pairwise detachably fastened to each other in an end-to-end fashion to jointly define an elongate receptacle having a continuous channel therewithin, wherein an uppermost tube of the plurality of tubes is configured to receive a lubricant sample which is extracted from a machine and which carries suspended particles associated with machine wear; and
a plurality filter patches carried by the receptacle, wherein each filter patch within the plurality of filter patches is disposed between pairwise fastened tubes for retaining at least a portion of the suspended particles upon being subjected to centrifugal force,
wherein pairwise fastened tubes are separable for removing or replacing a filter patch disposed therebetween; and
a centrifuge for simultaneously centrifuging the plurality of receptacles to displace a lubricant sample within each receptacle along the length of the channel of each receptacle.

19. The method as in claim 2, wherein pairwise fastened tubes are fastened by way of a threaded-fastening mechanism.

20. The method as in claim 2, wherein a bottom-most tube includes a base sealed with a drain plug.

21. The method as in claim 2, wherein a filter patch positioned closest to the uppermost tube has a larger pore size relative to each filter patch positioned further away from the uppermost tube.

22. The system as in claim 11, wherein pairwise fastened tubes are fastened by way of a threaded fastening mechanism.

23. The system as in claim 11, wherein a filter patch positioned closest to the uppermost tube has larger pore size relative to each filter patch positioned further away from the uppermost tube.

24. The system as in claim 11, wherein each filter patch within the plurality of filter patches has a pore size between 2.5 and 25 micrometers.

25. The system as in claim 11, wherein each filter patch within the plurality of filter patches has a pore size between 800 and 1200 micrometers.

* * * * *